(12) United States Patent
Fujinaka et al.

(10) Patent No.: US 8,846,327 B2
(45) Date of Patent: Sep. 30, 2014

(54) METHOD OF QUANTIFYING AUTOINDUCER-2

(75) Inventors: Hidetake Fujinaka, Haga-gun (JP); Keiko Kawasaki, Haga-gun (JP); Junji Nakamura, Haga-gun (JP)

(73) Assignee: Kao Corporation, Tokyo (JP)

( * ) Notice: Subject to any disclaimer, the term of this patent is extended or adjusted under 35 U.S.C. 154(b) by 716 days.

(21) Appl. No.: 12/738,185

(22) PCT Filed: Oct. 17, 2008

(86) PCT No.: PCT/JP2008/068876
§ 371 (c)(1),
(2), (4) Date: Apr. 15, 2010

(87) PCT Pub. No.: WO2009/051232
PCT Pub. Date: Apr. 23, 2009

(65) Prior Publication Data
US 2010/0233742 A1    Sep. 16, 2010

(30) Foreign Application Priority Data

Oct. 17, 2007    (JP) ................................. 2007-270587

(51) Int. Cl.
| | | |
|---|---|---|
| G01N 21/76 | (2006.01) | |
| C12Q 1/02 | (2006.01) | |
| G01N 33/487 | (2006.01) | |
| C12Q 1/66 | (2006.01) | |
| C07K 14/195 | (2006.01) | |

(52) U.S. Cl.
CPC .............. *C12Q 1/02* (2013.01); *C12Q 2304/60* (2013.01); *G01N 2333/28* (2013.01); *C12Q 1/66* (2013.01); *C07K 14/195* (2013.01)

USPC .................................... 435/8; 435/29; 436/93

(58) Field of Classification Search
None
See application file for complete search history.

(56) References Cited

U.S. PATENT DOCUMENTS

| | | | | |
|---|---|---|---|---|
| 6,559,176 | B1 * | 5/2003 | Bassler et al. | 514/408 |
| 6,599,715 | B1 * | 7/2003 | Vanderberg et al. | 435/34 |
| 6,703,513 | B1 * | 3/2004 | Quay | 549/229 |
| 6,720,415 | B2 | 4/2004 | Bassler et al. | |
| 6,780,890 | B2 * | 8/2004 | Bassler et al. | 514/562 |
| 6,844,423 | B2 * | 1/2005 | Bassler et al. | 530/350 |
| 6,864,067 | B2 * | 3/2005 | Bassler et al. | 530/350 |
| 6,936,435 | B2 * | 8/2005 | Bassler et al. | 435/32 |

(Continued)

FOREIGN PATENT DOCUMENTS

| | | |
|---|---|---|
| JP | 2003-526327 | 9/2003 |
| WO | WO 00/32152 | 6/2000 |
| WO | WO 01/85664 A2 | 11/2001 |

OTHER PUBLICATIONS

Winzer, K., et al., 2002, "LuxS: Its role in central metabolism and the in vitro synthesis of 4-hydroxy-5-methyl-3(2H)-furanone", Microbiology, vol. 148, No. 4, pp. 909-922.*

(Continued)

*Primary Examiner* — Manjunath Rao
*Assistant Examiner* — William W Moore
(74) *Attorney, Agent, or Firm* — Sterne, Kessler, Goldstein & Fox P.L.L.C.

(57) ABSTRACT

A method of quantifying autoinducer-2, including the steps of:
preparing a calibration curve using 4-hydroxy-5-methyl-3 (2H)-furanone as a standard sample; and
quantifying autoinducer-2 in a test sample based on the calibration curve prepared.

5 Claims, 3 Drawing Sheets

(56) References Cited

U.S. PATENT DOCUMENTS

| | | | |
|---|---|---|---|
| 6,942,986 B2* | 9/2005 | Bassler et al. | 435/32 |
| 7,183,099 B2* | 2/2007 | Taga et al. | 435/252.33 |
| 7,323,340 B2* | 1/2008 | Bassler et al. | 435/471 |
| 7,326,542 B2* | 2/2008 | Bassler et al. | 435/32 |
| 7,498,292 B2* | 3/2009 | Suga et al. | 506/15 |
| 7,846,422 B2* | 12/2010 | Oshino et al. | 424/49 |
| 8,293,478 B2* | 10/2012 | Souno et al. | 435/6.15 |
| 2003/0022932 A1* | 1/2003 | Surette et al. | 514/473 |
| 2005/0187190 A1 | 8/2005 | Vasu et al. | |
| 2005/0255444 A1* | 11/2005 | Van Der Meer | 435/4 |
| 2006/0063721 A1* | 3/2006 | Miller et al. | 514/23 |
| 2006/0269951 A1* | 11/2006 | Taga et al. | 435/6 |
| 2006/0275771 A1* | 12/2006 | Suzuki et al. | 435/6 |
| 2011/0124522 A1* | 5/2011 | Marrs et al. | 506/10 |
| 2012/0276546 A1* | 11/2012 | Souno et al. | 435/6.13 |

OTHER PUBLICATIONS

Hauck, T., et al., 2003, "Alternative pathway for the formation of 4,5-dihydroxy-2,3-pentanedione, the proposed precursor of 4-hydroxy-5-methyl-3(2H)-furanone as well as autoinducer-2, and its detection as natural constituent of tomato fruit", Biochimica et Biophysica Acta, vol. 1623, Nos. 2-3, pp. 109-119.*

Carter, G. P., et al., 2005, "Quorum sensing in Clostridium difficile: analysis of a luxS-type signalling system", Journal of Medical Microbiology, vol. 54, No. 2, pp. 119-127.*

Lowery, C. A., et al., 2005, "Quorum sensing in *Vibrio harveyi*: probing the specificity of the LuxP binding sites", Bioorganic & Medicinal Chemistry Letters, vol. 15, pp. 2395-2398.*

International Search Report for PCT/JP2008/068876, mailed Nov. 11, 2008 from the Japanese Patent Office, Tokyo, Japan.

International Preliminary Report on Patentability including the Written Opinion for PCT/JP2008/068876, issued May 11, 2010 from the International Bureau of WIPO, Geneva, Switzerland.

Intercellular signalling in *Vibrio harveyi*: sequence and function of genes regulating expression of luminescence BL Bassler et al., Mol Microbiol, Aug. 1993; 9(4): 773-786.

Multiple signalling systems controlling expression of luminescence in *Vibrio harveyi*: sequence and function of genes encoding a second sensory pathway BL Bassler, et al., Mol Microbiol, Jul. 1994; 13(2): 273-286.

Cross-species induction of luminescence in the quorum-sensing bacterium *Vibrio harveyi* BL Bassler, et al., J. Bacteriol., Jun. 1997; 179: 4043-4045.

Constraints on detection of autoinducer-2 (AI-2) signalling molecules using *Vibrio harveyi* as a reporter Sigrid C. J. DeKeersmaecker et al., Microbiology, Aug. 2003; 149: 1953-1956.

Chemical Synthesis of (*S*)-4,5-Dihydroxy-2,3-pentanedione, a Bacterial Signal Molecule Precursor, and Validation of Its Activity in *Salmonella typhimurium* Sigrid C. J. De Keersmaecker, et al., J. Biol. Chem., May 2005; 280: 19563-19568.

The LuxS family of bacterial autoinducers: biosynthesis of a novel quorum-sensing signal molecule. S Schauder, et al., Mol Microbiol, Jul. 2001; 41(2): 463-476.

Interference with AI-2-mediated bacterial cell-cell communication. KB Xavier et al., NIH Public Access Author Manuscript published in final edited form as Nature, Sep. 2005; 437(7059): 750-753.

Extended European Search report for EPO Application No. 08839699.9, mailed Feb. 16, 2011, European Patent Office, Rijswijk, Netherlands.

Rajamani, S. et al., "A LuxP-FRET-Based Reporter for the Detection and Quantification of AI-2 Bacterial Quorum-Sensing Signal Compounds," Biochemistry 46:3990-3997 (Apr. 2007), American Chemical Society, Washington, DC.

"Notice of Reasons for Rejection" (excerpted English translation) for JP Patent Appl. No. 2008-269049, date of dispatch: Feb. 12, 2013, Japanese Patent Office, Tokyo, Japan.

* cited by examiner

METHOD OF QUANTIFYING AUTOINDUCER-2

TECHNICAL FIELD

The present invention relates to a method of quantifying autoinducer-2, and a method of screening an autoinducer-2 regulator.

BACKGROUND ART

In nature, microorganisms have to live in a variety of environments. Microorganisms are forced to survive under poor nutrition, low temperature, high temperature, and pH change, and particularly in a living body, under the presence of phagocytes or antibacterial humoral factors (such as complements, antibodies, and lysozyme). In such circumstances, bacteria have acquired a mechanism for acutely sensing changes of the growth environments. It has been clarified that, as one of such mechanisms, microorganisms sense their concentrations in the environments via specific signaling substances and cleverly control a variety of their bioactivities depending on the concentrations. Such intercellular signaling mechanism is referred to as a quorum sensing system.

The quorum sensing has been reported for the first time in luminescent marine bacteria, *Vibrio fischeri* and *Vibrio harveyi*. However, in recent years, the quorum sensing is recognized as a general gene regulatory mechanism in a variety of bacteria. This phenomenon enables bacteria to concurrently show activities such as bioluminescence, swarming, formation of biofilms, production of proteases, synthesis of antibiotics, development of gene-recipient ability, plasmid conjugational transfer, production of pathogenic factors, and spore formation.

A bacterium having a quorum sensing system synthesizes and releases a signaling molecule, called an autoinducer, and controls gene expression as a function of cell density in response to the signaling molecule. So far, acyl homoserine lactone has been identified as autoinducer-1, and 4,5-dihydroxy-2,3-pentanedione has been identified as autoinducer-2.

It has been reported that clinically important bacteria, such as *Vibrio* bacteria, *Pseudomonas aeruginosa, Serratia* and *Enterobacter*, use autoinducer-1 for the quorum sensing. It has also been reported that *Vibrio harveyi* uses autoinducer-1, which has high species specificity, for intraspecific communication and uses autoinducer-2, which has low species specificity, for interspecific communication (see, for example, Bassler et al., Bacteriol. 179, pp. 4043-4045, 1997).

Recent studies further show that production of pathogenic factors is regulated by interspecific quorum sensing of pathogenic bacteria using autoinducer-2 (see, for example, Xavier KB. et al., Nature, 437, pp. 750-753, 2005). Therefore, it is required to quantify autoinducer-2 and identify a compound which inhibits the autoinducer-2 activity.

As a method of quantifying autoinducer-2, a bioassay using a bacterium which recognizes an autoinducer followed by emitting light was reported, and a reporter strain of *Vibrio harveyi* which can emits light in response to only autoinducer-2 was constructed (see, for example, Bassler et al., Mol. Microbiol., 9, pp. 773-786, 1993; and Bassler et al., Mol. Microbiol., 13, pp. 273-286, 1994). To quantify autoinducer-2 by a bioassay using such a bacterium, it is necessary to prepare a calibration curve using a standard sample. However, autoinducer-2 to be measured has an unstable structure and is difficult to obtain, therefore, it is unrealistic to use autoinducer-2 as a standard sample for preparing the calibration curve. Therefore, conventional measurement of autoinducer-2 provides only relative values.

Keersmaecker et al., J. Biol. Chem., 280, 20, pp. 19563-19568, 2008 describes that 4-hydroxy-5-methyl-3(2H)-furanone (hereinafter, also referred to as "HMF") has an autoinducer-2 activity. However, it is shown that the above-mentioned bioassay, which uses the reporter strain of *Vibrio harveyi*, can detect the activity at a considerably higher concentration of HMF as compared to 4,5-dihydroxy-2,3-pentanedione (DPD), which is used as autoinducer-2. Therefore, HMF has been considered to be inappropriate as a standard substance for quantifying autoinducer-2.

DISCLOSURE OF INVENTION

According to the present invention, there can be provided a method of quantifying autoinducer-2. In addition, according to the present invention, there can be provided a method of screening an autoinducer-2 regulator. Further, according to the present invention, there can be provided a method of measuring the autoinducer-2-regulating activity of the autoinducer-2 regulator.

The inventors of the present invention have made extensive studies, and as a result, the inventors have found that autoinducer-2 can be quantitatively measured by preparing a calibration curve using 4-hydroxy-5-methyl-3(2H)-furanone, which is a metabolite of autoinducer-2, as a standard sample. The present invention has been completed based on the above finding.

The method of quantifying autoinducer-2 of the present invention is a method of quantifying autoinducer-2, comprising the steps of:

preparing a calibration curve using 4-hydroxy-5-methyl-3 (2H)-furanone as a standard sample, and quantifying autoinducer-2 in a test sample based on the calibration curve prepared.

The method of screening autoinducer-2 of the present invention comprises quantifying autoinducer-2 by the above-mentioned method of quantifying autoinducer-2.

Further, a kit for quantifying autoinducer-2 of the present invention contains a standard sample containing 4-hydroxy-5-methyl-3(2H)-furanone in a known concentration, a reporter bacterium or a processed product thereof which recognizes autoinducer-2 followed by emitting light, and a calibration curve showing a correlation between concentrations of 4-hydroxy-5-methyl-3(2H)-furanone and autoinducer-2 for inducing the same photogenesis (light-emission) intensity.

A kit for screening an autoinducer-2 regulator of the present invention contains a standard sample containing 4-hydroxy-5-methyl-3(2H)-furanone in a known concentration, a reporter bacterium or a processed product thereof which recognizes autoinducer-2 followed by emitting light, and a calibration curve showing a correlation between concentrations of 4-hydroxy-5-methyl-3(2H)-furanone and autoinducer-2 for inducing the same photogenesis intensity.

Further, the method of measuring an autoinducer-2-regulating activity of the autoinducer-2 regulator of the present invention comprises the steps of:

d) bringing 4-hydroxy-5-methyl-3(2H)-furanone in a known concentration into contact with a reporter bacterium or a processed product thereof which recognizes autoinducer-2 followed by emitting light, measuring the photogenesis intensity, and preparing a calibration curve which shows a correlation between a concentration of 4-hydroxy-5-methyl-3 (2H)-furanone and the photogenesis intensity;

e) bringing autoinducer-2 and an autoinducer-2 regulator in known concentrations into contact with a reporter bacterium or a processed product thereof, and measuring the photogenesis intensity; and f) measuring the autoinducer-2-regulating activity of the autoinducer-2 regulator from the photogenesis intensity value obtained in the step e) based on the calibration curve obtained in the step d).

Accordingly, the invention includes the following Methods 1-14 and Kits 1-4.

(Method 1) A method of quantifying autoinducer-2, comprising the steps of: preparing a calibration curve using 4-hydroxy-5-methyl-3(2H)-furanone as a standard sample; and quantifying autoinducer-2 in a test sample based on the calibration curve prepared.

(Method 2) The method of quantifying autoinducer-2 according to Method 1, wherein the method is a bioassay for measuring a photogenesis intensity of a reporter bacterium or a processed product thereof which recognizes autoinducer-2 followed by emitting light.

(Method 3) The method of quantifying autoinducer-2 according to Method 2, wherein, in quantification by the bioassay for measuring the photogenesis intensity of the reporter bacterium or the processed product thereof which recognizes autoinducer-2 followed by emitting light, the calibration curve is prepared using 4-hydroxy-5-methyl-3(2H)-furanone as a standard sample and shows a correlation between a concentration of 4-hydroxy-5-methyl-3(2H)-furanone and the photogenesis intensity of the reporter bacterium or the processed product thereof.

(Method 4) The method of quantifying autoinducer-2 according to Method 2 or 3, wherein the reporter bacterium is a bacterium having an autoinducer-2 receptor and luciferase.

(Method 5) The method of quantifying autoinducer-2 according to any one of Methods 2 to 4, wherein the reporter bacterium is *Vibrio harveyi*.

(Method 6) The method of quantifying autoinducer-2 according to any one of Methods 2 to 5, comprising the steps of:
   a) bringing 4-hydroxy-5-methyl-3(2H)-furanone in a known concentration into contact with the reporter bacterium or the processed product thereof, measuring a photogenesis intensity, and preparing the calibration curve which shows a correlation between a concentration of 4-hydroxy-5-methyl-3(2H)-furanone and the photogenesis intensity;
   b) bringing a test sample into contact with the reporter bacterium or the processed product thereof and measuring a photogenesis intensity; and
   c) quantifying autoinducer-2 from a measurement value of the photogenesis intensity obtained in the step b) based on the calibration curve obtained in the step a).

(Method 7) The method of quantifying autoinducer-2 according to Method 6, wherein autoinducer-2 is quantified using, in the step c), two calibration curves including the calibration curve obtained in the step a) and a calibration curve showing a correlation between concentrations of 4-hydroxy-5-methyl-3(2H)-furanone and autoinducer-2 for inducing the same photogenesis intensity.

(Method 8) The method of quantifying autoinducer-2 according to any one of Methods 1 to 7, further comprising a step of removing contaminants from the test sample.

(Method 9) The method of quantifying autoinducer-2 according to any one of Methods 1 to 8, wherein the sample is prepared and/or preserved using a container to which the sample is adsorbed at a low degree.

(Method 10) The method of quantifying autoinducer-2 according to Method 9, wherein the container to which the sample is adsorbed at a low degree is a glass container.

(Method 11) The method of quantifying autoinducer-2 according to any one of Methods 1 to 10, wherein the calibration curve is prepared using a container to which the sample is adsorbed at a low degree.

(Method 12) The method of quantifying autoinducer-2 according to Method 11, wherein the container to which the sample is adsorbed at a low degree is a glass container.

(Method 13) A method of screening an autoinducer-2 regulator, comprising quantifying autoinducer-2 by the method according to any one of Methods 1 to 12.

(Kit 1) A kit for quantifying autoinducer-2 comprising: a standard sample containing 4-hydroxy-5-methyl-3(2H)-furanone in a known concentration; a reporter bacterium or a processed product thereof which recognizes autoinducer-2 followed by emitting light; and a calibration curve showing a correlation between concentrations of 4-hydroxy-5-methyl-3(2H)-furanone and autoinducer-2 for inducing the same photogenesis intensity.

(Kit 2) A kit for screening an autoinducer-2 regulator comprising: a standard sample containing 4-hydroxy-5-methyl-3(2H)-furanone in a known concentration; a reporter bacterium or a processed product thereof which recognizes autoinducer-2 followed by emitting light; and a calibration curve showing a correlation between concentrations of 4-hydroxy-5-methyl-3(2H)-furanone and autoinducer-2, for inducing the same photogenesis intensity.

(Kit 3) The kit according to Kit 1 or 2, further comprising a container to which the sample is adsorbed at a low degree.

(Kit 4) The kit according to Kit 3, wherein the container to which the sample is adsorbed at a low degree is a glass container.

(Method 14) A method of measuring an autoinducer-2-regulating activity of an autoinducer-2 regulator, comprising the steps of:
   d) bringing 4-hydroxy-5-methyl-3(2H)-furanone in a known concentration into contact with a reporter bacterium or a processed product thereof which recognizes autoinducer-2 followed by emitting light, measuring a photogenesis intensity, and preparing a calibration curve which shows a correlation between a concentration of 4-hydroxy-5-methyl-3(2H)-furanone and the photogenesis intensity;
   e) bringing autoinducer-2 and an autoinducer-2 regulator in known concentrations into contact with a reporter bacterium or a processed product thereof, and measuring a photogenesis intensity; and
   f) measuring an autoinducer-2-regulating activity of the autoinducer-2regulator from a photogenesis intensity value obtained in the step e) based on the calibration curve obtained in the step d).

Figure 1:
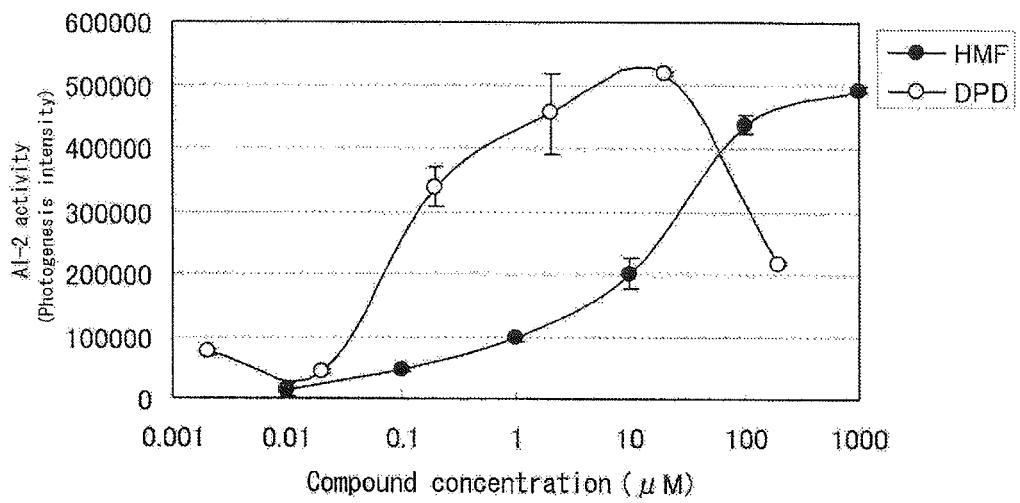
FIG. 1 illustrates correlations between a concentration of an HMF authentic preparation and a photogenesis intensity, and between a concentration of a DPD authentic preparation and a photogenesis intensity.

Other and further features and advantages of the invention will appear more fully from the following description, appropriately referring to the accompanying drawings.

BEST MODE FOR CARRYING OUT THE INVENTION

The present invention relates to a method of quantifying autoinducer-2, comprising the steps of:

preparing a calibration curve using 4-hydroxy-5-methyl-3(2H)-furanone as a standard sample; and quantifying autoinducer-2 in a test sample based on the calibration curve prepared.

Autoinducer-2 (hereinafter, also referred to as "AI-2") in the present invention is not particularly limited, but examples thereof include 4,5-dihydroxy-2,3-pentanedione (DPD) represented by the formula (I) described below.

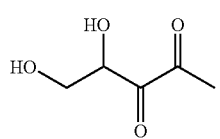

(I)

Autoinducer-2 represented by the formula (I) takes in boron at the time of bounding to an autoinducer-2 receptor of a bacterium and is converted into a furanosyl borate diester represented by the formula (II) described below.

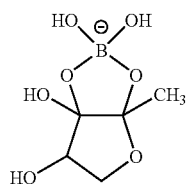

(II)

In the present invention, autoinducer-2 includes the furanosyl borate diester represented by the formula (II) described above.

The above-mentioned autoinducer-2 has an unstable structure and is hard to preserve, and it is not easy to obtain autoinducer-2 as a reagent. Therefore, it is difficult to use autoinducer-2 as a standard sample.

4-Hydroxy-5-methyl-3(2H)-furanone (HMF) is represented by the formula (III) described below and is produced by a structural change of autoinducer-2 represented by the formula (I) at the time of being metabolized.

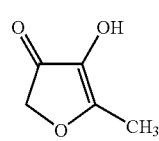

(III)

HMF has an autoinducer-2 activity and is stable unlike autoinducer-2, and commercially available HMF can be easily obtained as a reagent. HMF is available from, for example, SIGMA-ALDRICH.

In the present invention, the autoinducer-2 activity is an autoinducer-2 activity to affect a bacterium having a quorum sensing system, namely, an activity to promote bacterial functions induced by the quorum sensing via autoinducer-2. By the autoinducer-2-mediated quorum sensing, bacteria are known to show photogenesis, swarming, formation of biofilms, production of proteases, synthesis of antibiotics, development of gene-recognizing ability, plasmid conjunctional transfer, production of pathogenic factors, spore formation, and the like. Therefore, the autoinducer-2 activity is, that is to say, an activity of a bacterium which recognizes autoinducer-2, i.e., a bacterium having an autoinducer-2 receptor, to show bioluminescence, swarming, formation of biofilms, production of proteases, synthesis of antibiotics, development of gene-recognizing ability, plasmid splicing transmission, production of pathogenic factors, and spore formation. In particular, in the present invention, the autoinducer-2 activity refers to an activity to produce a pathogenic factor in a bacterium.

Examples of the pathogenic factor in a bacterium include, but not limited to, enterotoxin, adenylate cyclase toxin, adhesin, alkaline protease, hemolysin toxin, anthrax toxin, APX toxin, α toxin, β toxin, δ toxin, C2 toxin, C3 toxin, botulinum toxin, submit of bundle forming pilus structure, C5A peptidase, cardiac toxin, chemotaxis, cholera toxin, ciliary body toxin, clostridial cell toxin, clostridial nerve toxin, collagen adhesion gene, cytolysin, emetic toxin, endotoxin, exfoliatin toxin, exotoxin, extracellular elastase, fibrinogen, fibronectin bonded protein, filamentous hemagglutinin, fimbriae, gelatinase, hemagglutinin, leukotoxin, lipoprotein signal peptidase, listeriolysin O, M protein, nerve toxin, nonfimbriae adhesins, edema factor, permease, pertussis toxin, phospholipase, pilus, pore-forming toxin, proline permease, serine protease, Shiga toxin, tetanus toxin, thiol activation cytolysin, trachea cytolysin, and urease.

One embodiment of the method of quantifying autoinducer-2 of the present invention is a method of quantifying autoinducer-2 by a bioassay, in which autoinducer-2 is quantified by the photogenesis intensity of a reporter bacterium or a processed product thereof which recognizes autoinducer-2 followed by emitting light. In the present invention, quantification of autoinducer-2 includes measurement of the autoinducer-2 activity. The method of quantifying autoinducer-2 of the present invention is particularly preferably used for measuring an activity to produce a pathogenic factor in a bacterium among the above-mentioned autoinducer-2 activities.

HMF has an autoinducer-2 activity, and therefore, as autoinducer-2, HMF is known to make the reporter bacterium emit light. However, the HMF-induced photogenesis intensity of the reporter bacterium is lower than the photogenesis intensity induced by autoinducer-2.

The reporter bacterium used in the present invention, which recognizes autoinducer-2 and emits light, is preferably a bacterium having an autoinducer-2 receptor and luciferase. In the case where the bacterium has autoinducer-1 as well, light caused by autoinducer-1 is also detected at the same time, thereby preventing measurement of light induced by autoinducer-2. Therefore, a bacterium having no autoinducer-1 receptor is preferably used as a reporter bacterium. The bacterium having luciferase means a bacterium which produces luciferase and expresses a luciferase activity.

The processed product of the reporter bacterium is not particularly limited as long as the product emits light when contacted with autoinducer-2. Specific examples of the processed product of the reporter bacterium include homogenates of bacterial cell, extracts of bacterial cell, dead bacterial cells, suspensions of bacterial cell, bacterial cell cultures, and supernatants of bacterial cell culture.

Examples of the bacterium having an autoinducer-2 receptor include *Vibrio* bacterium, *Pseudomonas* bacterium, *Porphyromonas* bacterium, *Yersinia* bacterium, *Escherichia* bacterium, *Salmonella* bacterium, *Haemophilus* bacterium, *Helicobacter* bacterium, *Bacillus* bacterium, *Borrelia* bacterium, *Neisseria* bacterium, *Campylobacter* bacterium, *Deinococcus* bacterium, *Mycobacterium* bacterium, *Enterococcus* bacterium, *Streptococcus* bacterium, *Shigella* bacterium, *Aeromonas* bacterium, *Eikenella* bacterium, *Clostridium* bacterium, *Staphylococcus* bacterium, *Lactobacillus* bacterium, *Actinobacillus* bacterium, *Actinomyces* bacterium, *Bacteroides* bacterium, *Capnocytophaga* bacterium, *Klebsiella* bacterium, *Halobacillus* bacterium, *Fusobacterium* bacterium, *Erwinia* bacterium, *Elbenella* bacterium, *Listeria* bacterium, *Mannheimia* bacterium, *Peptococcus* bacterium, *Prevotella* bacterium, *Proteus* bacterium, *Serratia* bacterium and *Veillonella* bacterium. Specific examples thereof include *Vibrio harveyi*, *Vibrio fischeri*, *Vibrio cholerae*, *Vibrio parahaemolyticus*, *Vibrio alginolyticus*, *Pseudomonas phosphoreum*, *Porphyromonas gingivalis*, *Yersinia enterocolitica*, *Escherichia coli*, *Salmonella typhimurium*, *Haemophilus influenzae*, *Helicobacter pylori*, *Bacillus subtilis*, *Borrelia burgfdorferi*, *Neisseria meningitidis*, *Neisseria gonorrhoeae*, *Yersinia pestis*, *Campylobacter jejuni*, *Deinococcus radiodurans*, *Mycobacterium tuberculosis*, *Enterococcus faecalis*, *Streptococcus pneumoniae*, *Streptococcus pyogenes*, *Streptococcus mutans*, *Staphylococcus aureus*, *Shigella flexneri*, *Shigella boydii*, *Bacillus cereus*, *Bacillus cubtilis*, *Aeromonas hydrophila*, *Salmonella enterica*, *Eikenella corroders*, *Helicobacter hepaticus*, *Clostridium perfringens*, *Staphylococcus haemolyticus*, *Lactobacillus gasseri*, *Lactobacillus acidophilus*, *Lactobacillus reuteri*, *Lactobacillus salivarius*, *Lactobacillus casei*, *Streptococcus sanguinis*, *Streptococcus anginosus*, *Streptococcus oralis*, *Streptococcus bovis*, *Streptococcus gordonii*, *Streptococcus mitis*, *Actinobacillus actinomycetemcomitans*, *Vivrio vulnificus*, *Vibrio mimicus*, *Vibrio anguillarum*, *Lactobacillus rhamnosus*, *Erwinia amylovora*, *Erwinia carotovara*, *Halabacilus halophilus*, *Serratia pymuthica*, *Serratia marcescens*, *Bacteroides fragilis*, *Bacteroides vulgatus*, *Bacteroides distasonis*, *Listeria monocytogenes*, *Staphylococcus epidermidis*, *Clostridium difficile*, *Aeromonas hydrophilia*, *Mannhemia haemolytica*, *Klebsiella pneumoniae*, *Bacillus anthracis*, *Campylobacter coli*, *Campylobacter rectus*, *Proteus mirabilis*, *Actinomyces naeslundii*, *Peptococcus anaerobius*, *Fusobacterium nucleatum*, *Veillonella parvula*, *Capnocytophaga sputigena*, *Prevotella intermedia* and *Photobacterium phosphoreum*.

The reporter bacterium which can be preferably used in the present invention is preferably *Vibrio harveyi*, *Vibrio fischeri*, and *Photobacterium phosphoreum*; more preferably *Vibrio harveyi*.

The reporter bacterium which is preferably used in the method of the present invention may be a bacterium produced by a genetic recombination technology. For example, a recombinant bacterium which is obtained by introducing an autoinducer-2 receptor gene and/or a luciferase gene into a host bacterium is preferably used. Examples of the recombinant bacterium include a bacterium obtained by introducing the luciferase gene into a host bacterium having an autoinducer-2 receptor, a bacterium obtained by introducing the autoinducer-2 receptor gene into a host bacterium having luciferase, and a bacterium obtained by introducing both the autoinducer-2 receptor gene and luciferase gene. Such recombinant bacteria can be obtained by ligating the above-mentioned genes to appropriate vectors and introducing the resultant recombinant vectors into a host bacterium so that the genes can be expressed.

A method of obtaining a desired gene from a bacterial genome is well known in the molecular biological field. For example, in the case where the sequence of the gene is known, a suitable genome library is prepared by restriction endonuclease digestion, and a probe having a sequence complementary to a desired gene sequence may be used for screening. After the sequence is isolated, DNA is amplified by a standard amplification method such as a polymerase chain reaction (PCR), to thereby obtain DNA in an amount suitable for transformation.

The vector to be used for introducing of a gene is not particularly limited as long as the vector can be replicated in a host cell, and examples thereof include plasmid DNA, phage DNA, and cosmid DNA. Examples of the plasmid DNA include pBR322, pSC101, pUC18, pUC19, pUC118, pUC119, pACYC117, pBluescript II SK(+), pETDuet-1 and pACYCDuet-1. Examples of the phage DNA include λgt10, Charon 4A, EMBL-, M13mp18 and M13mp19. The host is not particularly limited as long as a desired gene can be expressed, and in general, the host is preferably a gram-negative bacterium. Examples thereof include *Vibrio* bacteria (such as *Vibrio harveyi* and *Vibrio fischen*) and *Escherichia* bacteria (such as *Escherichia coli*).

Examples of the autoinducer-2 receptor include LuxP and Lsr. The base sequence of the LuxP gene is registered as, for example, Accession No: NC_009654, NZ_AAWP01000010, NZ_AAWQ01000010, NZ_AAWG01000046, NZ_AAWF01000001, NZ_AAWE01000001, NZ_AAWD01000069, NZ_AAUU01000006, NZ_AAUS01000001, NZ_AAUR01000051, CP000749, DS265228, DS265359, AAWQ01000010, AAWF01000001, AAWP01000010, AAWG01000046, NC_009456, BA000032, CP000626, AE003853, AAWE01000001, AAWD01000069, DS179735, DS179611, AAUU01000006, AAUS01000001, AAUR01000051, NZ_AAKJ02000001, AAKJ02000001, NZ_AAUT01000001, AAUT01000001, AB086408, AB086229, DQ775944, NZ_AAPS01000004, AAPS01000004, NC_006840, AB113244, NZ_AANE01000009, AANE01000009, NZ_AANE01000021, AANE01000021, NC_004605, AY962288, CP000020, VHU07069, and X54690 in a published database (GenBank, EMBL, and DDBJ). The base sequence of the Lsr gene is also registered as NC_000913, U00096, NC_005126, and the like. Examples of the luciferase gene include luciferase genes derived from organisms such as insects such as firefly, luminous bacteria such as luminescent marine bacteria, marine coleopteran, and algae.

To prepare a bacterium having no autoinducer-1 receptor, a recombinant bacterium having a knockout of the autoinducer-1 receptor gene may be prepared. The recombinant bacterium having a knockout of the autoinducer-1 receptor gene means a bacterium which has a disrupted autoinducer-1 receptor gene and cannot express the gene. Examples of a gene knockout method include a method of disrupting a target gene using a vector which causes homologous recombination at any position in the target gene (targeting vector) (gene-targeting method) and a method involving inserting a trap vector (a reporter gene having no promoter) at any position in a target gene, thereby disrupting the gene and eliminating its functions.

As recombinant bacteria which can be suitably used in the method of the present invention, strains of *Vibrio harveyi* (BB170 and MM32 strains) which can respond to only auto-inducer-2 and emit light can be preferably used (see, for example, Bassler et al., Mol. Microbial., 9, pp. 773-786, 1993; and Bassler et al., Mol. Microbial., 13, pp. 273-286, 1994).

The inventors of the present invention have found that the photogenesis intensity of a reporter bacterium induced by HMF has a high correlation with the photogenesis intensity of a bacterium induced by autoinducer-2 (in particular, 4,5-dihydroxy-2,3-pentanedione). In the method of quantifying autoinducer-2 of the present invention, a calibration curve is prepared using 4-hydroxy-5-methyl-3(2H)-furanone as a standard sample and autoinducer-2 in a test sample is quantified based on the calibration curve prepared. The above-mentioned calibration curve prepared using 4-hydroxy-5-methyl-3(2H)-furanone as a standard sample preferably illustrates a correlation between the concentration of 4-hydroxy-5-methyl-3(2H)-furanone and the photogenesis intensity of a reporter bacterium which recognizes autoinducer-2 followed by emitting light.

More specifically, the method of quantifying autoinducer-2 of the present invention preferably comprises the following steps a) to c):

a) bringing 4-hydroxy-5-methyl-3(2H)-furanone in a known concentration into contact with the reporter bacterium or the processed product thereof, measuring the photogenesis intensity, and preparing the calibration curve which illustrates a correlation between a concentration of 4-hydroxy-5-methyl-3(2H)-furanone and the photogenesis intensity;

b) bringing a test sample into contact with the reporter bacterium or the processed product thereof and measuring a photogenesis intensity; and c) quantifying autoinducer-2 from a measurement value of the photogenesis intensity obtained in the step b) based on the calibration curve obtained in the step a).

Bringing 4-hydroxy-5-methyl-3(2H)-furanone used as a standard sample or a test sample into contact with a reporter bacterium or a processed product thereof includes culturing the reporter bacterium in the presence of the standard sample or test sample. In this case, culture conditions of the reporter bacterium are not particularly limited, but in general, culture is performed under aerobic conditions such as shaking culture or aeration and stirring culture at a temperature of preferably 10 to 40° C., more preferably 20 to 37° C. for preferably 1 to 10 hours, more preferably 2 to 6 hours. Measurement of the photogenesis intensity may be performed after culture by measuring, for example, the photogenesis intensity of a culture medium, a culture supernatant, a bacterial cell homogenate, a bacterial cell suspension, or a bacterial cell extract.

The test sample is not particularly limited, but examples thereof include extracts of animals (including microorganisms such as fungi and actinomycetes) and plants, compounds, and artificially synthesized products.

The calibration curve which illustrates a correlation between the concentration of 4-hydroxy-5-methyl-3(2H)-furanone and the photogenesis intensity is prepared by bringing different concentrations of 4-hydroxy-5-methyl-3(2H)-furanone into contact with a reporter bacterium, measuring the photogenesis intensity and plotting the photogenesis intensity measured for the concentration of 4-hydroxy-5-methyl-3(2H)-furanone. Measurement of the photogenesis intensity can be performed using a measuring instrument generally used in this technical field, for example, a chemiluminescence analyzer.

Quantification of autoinducer-2 in the step c) is preferably performed using two calibration curves including the calibration curve obtained in the step a) (referred to as primary calibration curve) and a calibration curve which shows a correlation between the concentrations of 4-hydroxy-5-methyl-3(2H)-furanone and autoinducer-2 for inducing the same photogenesis intensity (referred to as secondary calibration curve). That is, preferably, the photogenesis intensity measured for the test sample in the step b) is once converted into the concentration of HMF based on the primary calibration curve, and the concentration of HMF is further converted into the concentration of autoinducer-2 based on the secondary calibration curve.

In the secondary calibration curve, the photogenesis intensity of HMF has a particularly high correlation with the photogenesis intensity of autoinducer-2 in an HMF concentration range of 0.01 to 10 µM and in a DPD concentration range of 0.01 to 0.1 µM. Therefore, the method of the present invention is particularly preferably used for quantification of autoinducer-2 in a concentration range of 0.01 to 0.1 µM and quantification of an autoinducer-2 activity which corresponds to the concentration.

In the method of the present invention, it is preferred to remove contaminants in a test sample before bringing the test sample into contact with a reporter bacterium or a processed product thereof. The method of removing contaminants is not particularly limited, but it is preferred to employ a method of removing high-molecular-weight contaminants to improve the purification degree of low-molecular-weight substances because autoinducer-2 has a low molecular weight. Therefore, removal of contaminants is preferably performed by filtration, and for example, removal of contaminants may be performed by ultrafiltration and microfiltration. In the present invention, contaminants are preferably removed by ultrafiltration. The fractionated molecular weight (molecular weight cutoff value) of an ultrafiltration membrane is generally 3000 or less, preferably 1000 or less. In the case where the cutoff value is low, the fractionation time is affected. Therefore, the membrane may be selected in consideration of working efficiency. By preliminarily removed contaminants, the purity of autoinducer-2 in a target sample increases, thereby achieving more precise quantification of autoinducer-2.

In the method of quantifying autoinducer-2 of the present invention, sample preparation and/or preservation is preferably performed using a container having low adsorbability to samples. In addition, preparation of a calibration curve is preferably performed using a container having low adsorbability to samples. In the present invention, the container having low adsorbability to samples means a container which less reduces the actions of AI-2 and/or HMF (a container which does not significantly decrease the autoinducer-2 activity). The material and surface treatment method of the container are not particularly limited as long as the container is that described above. Examples of the container having low adsorbability include glass containers, metallic containers, containers having a surface treated with a fluorine compound, and siliconized plastic containers, and the glass container are particularly preferably used.

In general biochemical experiments, plastic containers such as disposal tubes are used because glass containers may adsorb a more variety of substances such as proteins. However, it was clarified that, in quantification of autoinducer-2, adsorption of autoinducer-2 and HMF to glass containers was more suppressed compared with that to plastic containers. The glass containers suppress adsorption of HMF, and therefore, when a calibration curve is prepared based on the use of glass containers, it is possible to detect HMF in a bioassay even when the concentration is 1 μM or less, further 0.1 μM or less. When using the glass container, it is possible to accurately prepare a calibration curve showing a correlation between the HMF concentration and the photogenesis intensity, and a calibration curve showing a correlation between concentrations of the HMF and the autoinducer-2 for inducing the same photogenesis intensity even within a low HMF concentration range of 1 μM or less, further 0.1 μM or less. Moreover, the glass containers suppress adsorption of autoinducer-2, and therefore, it is possible to detect and quantify a low concentration of autoinducer-2 by preparing and/or preserving test samples in the glass containers.

A generally used glass container may be used as the glass container, and for example, there may be used containers made of glass materials such as glass, quartz glass, molten quartz, synthetic quartz, alumina, sapphire, ceramics, forsterite, and photosensitive glass.

Conventional measurement of autoinducer-2 is conducted by a bioassay in which measurement values vary depending on the type of a reporter bacterium, type of a medium, pH, and temperature. Therefore, so far the measurement of autoinducer-2 provided only relative values. However, in the present invention, the concentration of autoinducer-2 and autoinducer-2 activity can be measured as absolute values because an easily available standard sample is used. Therefore, according to the present invention, it is possible to compare values determined from the photogenesis intensities measured under different conditions as absolute values. In addition, it is possible to save the effort of measuring target samples in a repetitive manner.

According to the method of quantifying autoinducer-2 of the present invention, it is possible to quantify the concentration of autoinducer-2 and measure the autoinducer-2 activity. Therefore, the autoinducer-2-regulating activity of an autoinducer-2 regulator can be measured by bringing known concentrations of autoinducer-2 and an autoinducer-2 regulator into contact with a reporter bacterium or a processed product thereof and measuring the photogenesis intensity, that is, in the step b) above, by bringing a test sample prepared by adding autoinducer-2 regulator to a sample containing a known amount of autoinducer-2 into contact with a reporter bacterium or a processed product thereof, and measuring the photogenesis intensity.

The autoinducer-2 regulator means a substance having an activity to regulate the autoinducer-2 activity, and includes an autoinducer-2 inhibitor which inhibits the autoinducer-2 activity and an autoinducer-2 promoter which promotes the autoinducer-2 activity.

In addition, it is possible to screen an autoinducer-2 regulator by bringing a known concentration of autoinducer-2 and a test sample into contact with a reporter bacterium or a processed product thereof, and measuring the photogenesis intensity, that is, in the step b) above, by bringing a test sample prepared by adding a test substance to a sample containing a known amount of autoinducer-2 into contact with a reporter bacterium or a processed product thereof and measuring the photogenesis intensity, and selecting a test substance which provides a change in the photogenesis intensity. In the screening method, the autoinducer-2-regulating activity of the test substance can also be measured.

In addition, the present invention relates to a kit for quantifying autoinducer-2 and a kit for screening an autoinducer-2 regulator. The kit of the present invention includes a standard sample containing a known concentration of 4-hydroxy-5-methyl-3(2H)-furanone, a reporter bacterium or a processed product thereof which recognizes autoinducer-2 followed by emitting light, and a calibration curve showing a correlation between concentrations of 4-hydroxy-5-methyl-3(2H)-furanone and autoinducer-2 for inducing the same photogenesis intensity. The kit of the present invention may further include a container for preparing and preserving samples, preferably a glass container; a container to be used for preparing the calibration curve, preferably a glass container; a filtration membrane, a buffer, and a sample diluent. The kit for screening an autoinducer-2 regulator may include, as a positive control, a known autoinducer-2 regulator, for example, known autoinducer-2 inhibitor and autoinducer-2 promoter. Examples of the known autoinducer-2 inhibitor include 3-phenyl-2-propenal, 2-pentyl-2-cyclopentene-1-one, 2-methoxy-2,4-diphenyl-3(2H)-furanone, 5-methyl-2-ethyl-4-hydroxy-3(2H)-furanone, and 2,5-dimethyl-4-hydroxy-3(2H)-furanone.

According to the present invention, it is possible to measure autoinducer-2 quantitatively. In addition, according to the present invention, it is possible to screen an autoinducer-2 regulator. Moreover, according to the present invention, it is possible to measure the autoinducer-2-regulating activity of an autoinducer-2 regulator.

The present invention will be described based on the following examples, but the invention is not intended to be limited thereto.

EXAMPLES (1) Preparation of Calibration Curve

Figure 2:
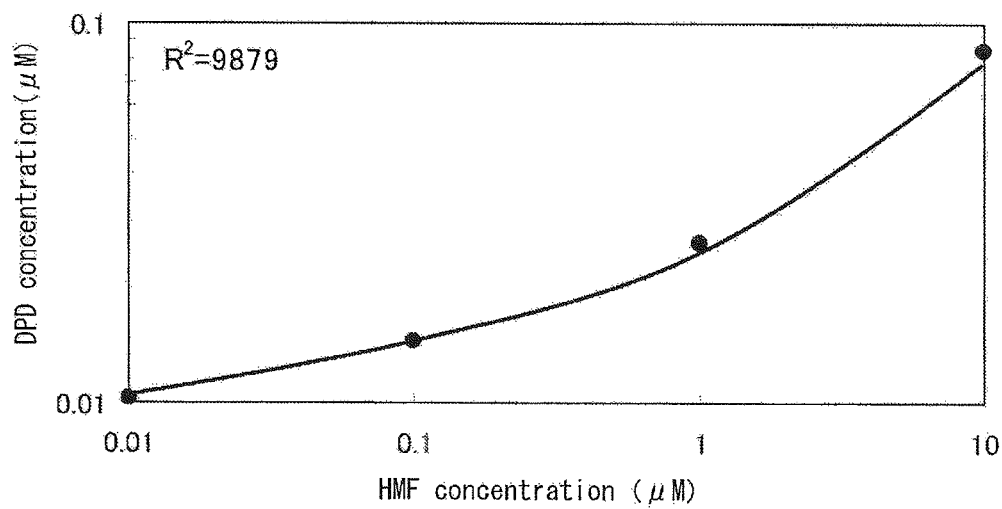
FIG. 2 illustrates a calibration curve prepared by plotting a correlation between an HMF concentration and a DPD concentration for inducing the same photogenesis intensity based on the results of FIG. 1.

An HMF authentic preparation (SIGMA) and a DPD authentic preparation (examination of synthesis was requested to OMM Scientific, and a product synthesized by the company was purchased) were added at a final concentration of 0.001 to 1000 μM to a *Vibrio harveyi* BB170 strain (purchased from ATCC, cultured under aerobic conditions at 30° C. in a marine medium (manufactured by Difco)) used as an autoinducer-2 (AI-2) reporter bacterium. The photogenesis intensity as the index of the AI-2 activity was measured in the same way as in Keersmaecker S. C. J. et al., J. Biol. Chem., 280(20), pp. 19563-19568, 2005. Namely, the *Vibrio harveyi* BB170 strain was diluted to 5000-fold as a final concentration with an AB medium (for example, see Bassler et al., Mol. Microbiol., 9, pp. 773-786, 1993), and the reporter bacterium liquid and the authentic preparations were mixed at a volume ratio of 9:1, followed by culturing with aerobic shaking at 30° C. Four hours later, the photogenesis intensity was measured using a chemiluminescence analyzer (Berthold, Mitharas LB940 (product name), detecting chemiluminescence). FIG. 1 illustrates a correlation between the concentrations of the HMF authentic preparation and DPD authentic preparation, and the photogenesis intensity. The HMF authentic preparation and DPD authentic preparation were prepared in glass containers. FIG. 2 illustrates a calibration curve prepared by plotting, based on the results of FIG. 1, a correlation between the HMF concentration and the DPD concentration, both of which show the same photogenesis intensity.

FIG. 2 indicates that the HMF concentration and the DPD concentration have a high correlation coefficient via the photogenesis intensity. Therefore, it was found that the quantification of the DPD concentration can be finally achieved by converting the photogenesis intensity of the reporter bacterium, measured in the presence of a test sample, into the HMF concentration based on the calibration curve prepared using HMF as a standard sample.

(2) Study on Containers for Sample Preparation and for Sample Preservation

Figure 3:
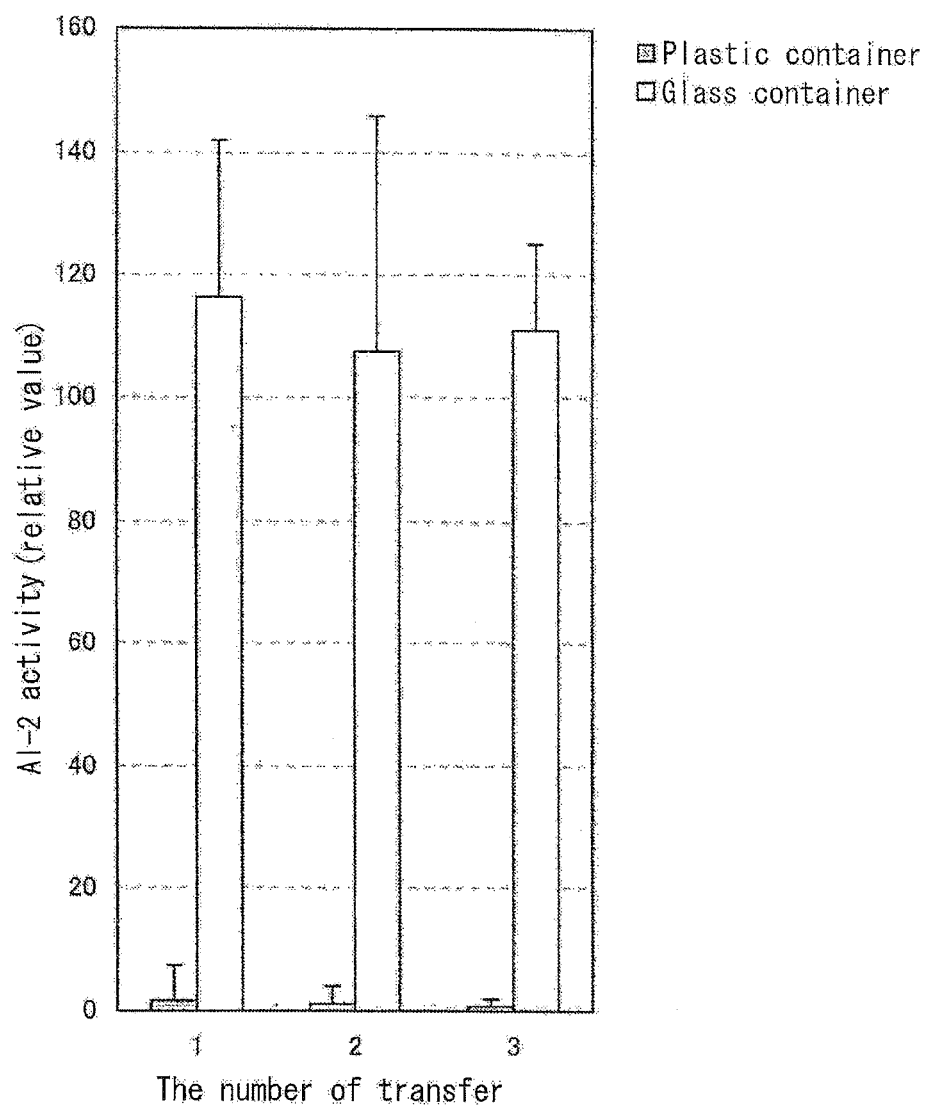
FIG. 3 illustrates the results obtained by partially purifying a culture supernatant of a *Vibrio harveyi* BB170 strain, placing the resultant as a sample in a plastic container or a glass container, and measuring the photogenesis intensity of a reporter bacterium in the sample every time the sample was transferred to another container.

A partially-purified product of a culture supernatant of a *Vibrio* harveyi BB170 strain was prepared as a sample and placed in a plastic container or glass container for general experiments, and the sample was transferred to a new container once to three times in a repetitive manner. With each sample transfer, the photogenesis intensity of the reporter bacterium in the sample measured as an index of the AI-2 activity in the same way as in (1) above. The photogenesis intensity of the sample before transferring the sample to another container was defined as 100, and the measurement values were shown as relative values. The results are shown in FIG. 3.

The AI-2 activity of a sample in a plastic container significantly decreased by transfer. On the other hand, the AI-2 activity of a sample in a glass container remained unchanged by transfer.

In general biochemical experiments, plastic containers such as disposal tubes are used because glass containers may adsorb a more variety of substances such as proteins. However, it was clarified that, in quantification of AI-2, adsorption of AI-2 to a glass container was more suppressed compared with that to a plastic container and the glass container was suitable for quantification of AI-2.

(3) Pretreatment of Test Sample

Figure 4:
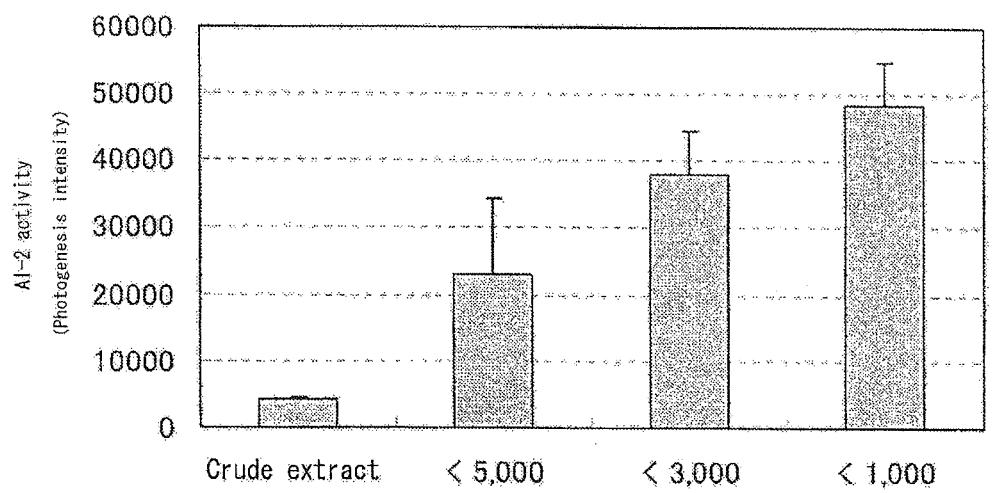
FIG. 4 illustrates the results of measurement of the autoinducer-2 activity of each ultrafiltrate obtained by ultrafiltrating (molecular weight cutoff values 5000, 3000, and 1000) a crude extract of a tongue coating specimen, based on the photogenesis intensity of a reporter bacterium as an index.

Human tongue coating was scraped using a commercially available tongue brush and washed with PBS by centrifugation (3000 rpm, 10 minutes, 4° C.), to thereby prepare a test sample. The tongue coating was resuspended in 1.5 ml PBS and subjected to ultrasonication (Branson, Sonifier 150 (product name), under ice-cooling, 1 minute×5 times) and centrifugation (4° C., 15,000 rpm, 10 minutes), to thereby obtain a crude extract. Moreover, the crude extract was subjected to ultrafiltration (molecular weight cutoff values 5000, 3000, and 1000) (Millipore, Microcon (product name)), the AI-2 activity of each ultrafiltrate was measured based on the photogenesis intensity of a reporter bacterium as an index in the same way as in (1) above. The results are shown in FIG. 4.

The smaller the cutoff value of ultrafiltration, the larger the AI-2 activity. Therefore, removal of high-molecular-weight contaminants is considered to improve the purification degree of DPD (molecular weight 132.11) having a low molecular weight, to thereby enable proper quantification of AI-2 in a test sample.

(4) Measurement of AI-2 Activity (Evaluation of AI-2 Activity Inhibitor)

Figure 5:
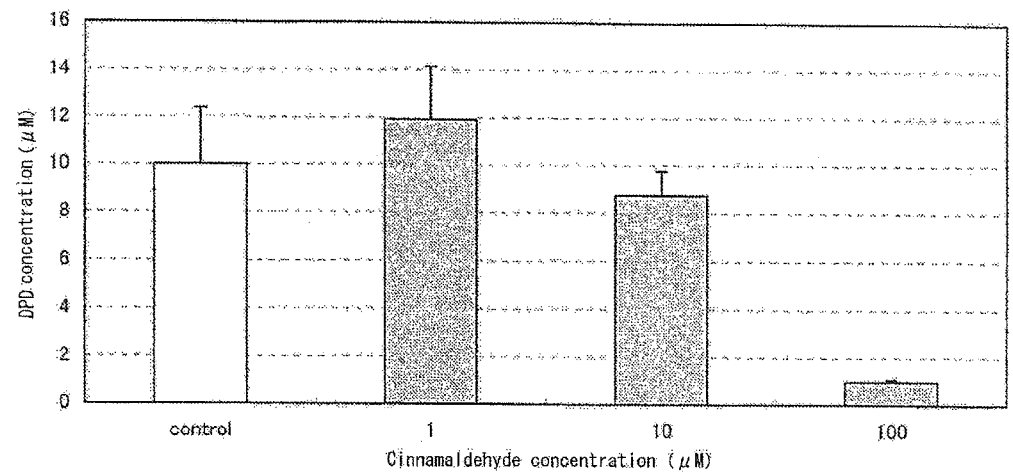
FIG. 5 illustrates the results of measurement of the autoinducer-2 activity using the calibration curve illustrated in FIG. 1 after pre-incubation of a *Vibrio harveyi* BB170 strain and a cinnamaldehyde authentic preparation followed by addition of DPD.

A *Vibrio harveyi* BB170 strain and a cinnamaldehyde authentic preparation (3-phenyl-2-propenal) (SIGMA) prepared at various concentration were pre-incubated, and DPD was added so that the final concentration was 10 µM. The AI-2 activity was measured using the calibration curve prepared in (1) above based on the photogenesis intensity of the reporter bacterium as an index. Namely, DPD concentration (µM) corresponding to the AI-2 activity was measured. The results are shown in FIG. 5.

Cinnamaldehyde is known to be a compound having an AI-2-inhibiting activity (for example, Niu C. et al., Lett. Appl. Microbiol., 43(5), pp. 489-494, 2006), and it was shown that the AI-2-inhibiting activity could be measured quantitatively by the method of the present invention. Therefore, it was shown that according to the present invention, it was possible to perform quantitative and precisive screening of an AI-2-regulating substance, by measuring the intensity of the AI-2-regulating activity of a test substance.

Industrial Applicability

According to the present invention, it is possible to quantify autoinducer-2 quantitatively. Therefore, the method of quantifying autoinducer-2 of the present invention can be suitably used for detecting a bacterium having a quorum sensing system.

Having described our invention as related to the present embodiments, it is our intention that the invention not be limited by any of the details of the description, unless otherwise specified, but rather be construed broadly within its spirit and scope as set out in the accompanying claims.

This non-provisional application claims priority under 35 U.S.C. §119 (a) on Patent Application No. 2007-270587 filed in Japan on Oct. 17, 2007, which is entirely herein incorporated by reference.

What is claimed is:

1. A method of quantifying the concentration of autoinducer-2 in a test sample, comprising the steps of:
    (a) bringing an increasing series of concentrations of 4-hydroxy-5-methyl-3(2H)-furanone (HMF) comprising a range from about 0.01 µM to about 10 µM into contact with a known concentration of a living reporter bacterium having an autoinducer-2 quorum sensing system and measuring the induced photogenesis activity by the intensity of light emitted when the reporter bacterium is contacted with HMF in a bioassay,
    (b) bringing an increasing series of concentrations of autoinducer-2, which is 4,5-dihydroxy-2,3-pentanedione (DPD), comprising a range from about 0.01 µM to about 0.1 µM into contact with a known concentration of the same living reporter bacterium of step (a) that has an autoinducer-2 quorum sensing system and measuring the induced photogenesis activity by the intensity of light emitted when the reporter bacterium is contacted with DPD in with a bioassay,
    (c) preparing a calibration curve that shows the correlation between said concentrations of said HMF induced photogenesis activity and said concentrations of said autoinducer-2/DPD induced photogenesis activity,
    (d) bringing a test sample into contact with the concentrations of the living reporter bacterium of steps (a) and (b) and measuring the autoinducer-2 induced photogenesis activity of the reporter bacterium that results from said contact with said test sample;
    (e) quantifying autoinducer-2 concentration in said test sample by converting the autoinducer-2 induced photogenesis activity obtained in step (d) into an HMF concentration based on the HMF calibration curve obtained in step (c), and
    (f) converting said HMF concentration of step (e) into the concentration of said autoinducer-2 in said test sample,
    wherein said steps (a), (b), and (d) are performed using containers to which the measured sample is adsorbed to a low degree such that the autoinducer-2 induced photogenesis activity that is measured in steps (a), (b) and (d) and is not significantly reduced by adsorption of the sample to the container.

2. The method of quantifying autoinducer-2 according to claim 1, wherein the reporter bacterium is *Vibrio harveyi*.

3. The method of quantifying autoinducer-2 according to claim 1, further comprising a step of removing contaminants from the test sample of step (d).

4. The method of quantifying autoinducer-2 according to claim 1, wherein before bringing the sample in step (d) into contact with the reporter bacterium, the sample was prepared and/or preserved in a container to which the sample is adsorbed at a low degree.

5. The method of quantifying autoinducer-2 according to claim 1, wherein the container to which the measured sample is adsorbed to a low degree is a glass container.

* * * * *